(12) United States Patent
Ravikumar et al.

(10) Patent No.: US 10,390,852 B2
(45) Date of Patent: Aug. 27, 2019

(54) MINIMALLY INVASIVE SURGICAL ASSEMBLY AND METHODS

(71) Applicant: MINI-LAP TECHNOLOGIES, INC., Dobbs Ferry, NY (US)

(72) Inventors: Sundaram Ravikumar, Briarcliff Manor, NY (US); Guy Osborne, Trumbull, CT (US); Harry Allan Alward, Shelton, CT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 363 days.

(21) Appl. No.: 14/784,844

(22) PCT Filed: Apr. 16, 2014

(86) PCT No.: PCT/US2014/034431
§ 371 (c)(1),
(2) Date: Oct. 15, 2015

(87) PCT Pub. No.: WO2014/172503
PCT Pub. Date: Oct. 23, 2014

(65) Prior Publication Data
US 2016/0058461 A1  Mar. 3, 2016

Related U.S. Application Data

(60) Provisional application No. 61/812,450, filed on Apr. 16, 2013.

(51) Int. Cl.
*A61B 17/29* (2006.01)
*A61B 17/28* (2006.01)
(Continued)

(52) U.S. Cl.
CPC .............. *A61B 17/29* (2013.01); *A61B 17/28* (2013.01); *A61B 17/3496* (2013.01);
(Continued)

(58) Field of Classification Search
CPC ..... A61B 17/28; A61B 17/29; A61B 17/3496; A61B 2017/2901; A61B 2017/2902; A61B 2017/2937; A61B 18/14; A61B 18/1447
(Continued)

(56) References Cited

U.S. PATENT DOCUMENTS 4,016,881 A * 4/1977 Rioux ................ A61B 18/1442
606/42
4,258,716 A * 3/1981 Sutherland ....... A61B 17/32001
606/170
(Continued)

FOREIGN PATENT DOCUMENTS

JP 2003299669 A 10/2003
KR 20090013169 A 2/2009

*Primary Examiner* — Michael F Peffley
*Assistant Examiner* — Khadijeh A Vahdat
(74) *Attorney, Agent, or Firm* — Baker & Hostetler LLP

(57) ABSTRACT

A surgical device includes an elongated needle body defining an interior lumen extending longitudinally therethrough, having a sharpened distal tip portion. The device further includes an assembly operatively associated with the interior lumen of the needle body. The assembly includes a shaft having an outer surface profile corresponding to an inner surface of the interior lumen of the needle body and a pair of arms extending distally from the shaft. The pair of arms are biased radially outward from the longitudinal axis of the shaft, and each of the pair of arms having a blunt front surface, wherein one of the arms is in a fixed axial alignment with the sharpened distal tip portion of the needle body such that the arms act as an obturator relative to the sharpened distal tip portion of the needle body to guard the needle body from causing accidental needle tip trauma.

15 Claims, 5 Drawing Sheets

(51) Int. Cl.
  *A61B 17/34* (2006.01)
  *A61B 18/14* (2006.01)
(52) U.S. Cl.
  CPC .. *A61B 18/1447* (2013.01); *A61B 2017/2901* (2013.01); *A61B 2017/2902* (2013.01); *A61B 2017/2937* (2013.01)
(58) Field of Classification Search
  USPC .......................... 606/51–52, 169, 205–207
  See application file for complete search history.

(56) References Cited

U.S. PATENT DOCUMENTS

| | | | |
|---|---|---|---|
| 5,290,276 A | | 3/1994 | Sewell, Jr. |
| 5,476,479 A | * | 12/1995 | Green ................... A61B 17/29 |
| | | | 606/205 |
| 5,626,597 A | * | 5/1997 | Urban ................... A61B 17/34 |
| | | | 606/159 |
| 6,969,389 B2 | | 11/2005 | Kidooka |
| 7,766,937 B2 | | 8/2010 | Ravikumar |
| 8,133,255 B2 | | 3/2012 | Ravikumar |
| 8,230,863 B2 | | 7/2012 | Ravikumar et al. |
| 8,313,507 B2 | | 11/2012 | Ravikumar |
| 2006/0089633 A1 | | 4/2006 | Bleich et al. |
| 2007/0213766 A1 | * | 9/2007 | Ravikumar .......... A61B 17/221 |
| | | | 606/205 |
| 2007/0250112 A1 | | 10/2007 | Ravikumar et al. |
| 2007/0282170 A1 | | 12/2007 | Ravikumar |
| 2008/0015631 A1 | | 1/2008 | Lee et al. |
| 2010/0016884 A1 | | 1/2010 | Ravikumar |
| 2010/0292724 A1 | | 11/2010 | Ravikumar et al. |
| 2011/0009850 A1 | | 1/2011 | Main et al. |

* cited by examiner

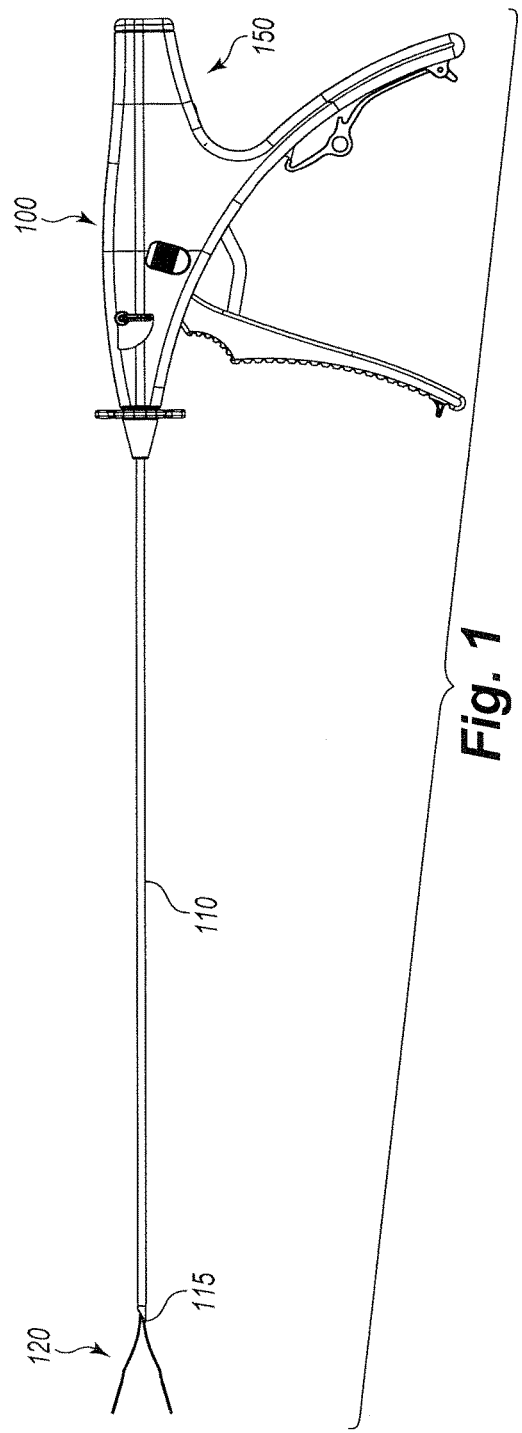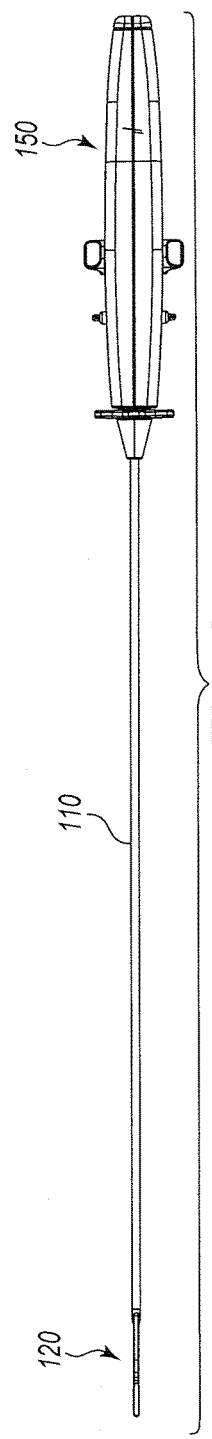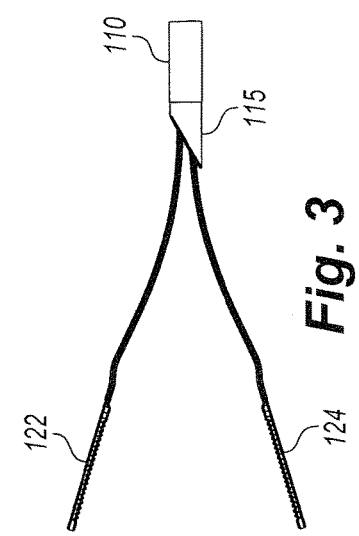

MINIMALLY INVASIVE SURGICAL ASSEMBLY AND METHODS

CROSS-REFERENCE TO RELATED APPLICATIONS

This application is a National Stage of International patent application PCT/US2014/034431, filed on Apr. 16, 2014, which claims priority to U.S. provisional patent application No. 61/812,450, filed on Apr. 16, 2013, the disclosures of which are incorporated by reference in their entirety.

BACKGROUND OF THE INVENTION

Field of the Invention

The present invention relates to surgical instruments and methods of their use, and more particularly to minimally invasive surgical instruments and methods incorporating working tool disposed within a needle and configured so that the needle extends and retracts over the working tool.

Description of Related Art

Over the last two decades, minimally invasive surgery has become the standard for many types of surgeries which were previously accomplished through open surgery. Minimally invasive surgery generally involves introducing an optical element (e.g., laparoscopic or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly.

The trocar assembly often includes a port, a sharp pointed element (trocar) extending through and beyond the distal end of the port, and at least in the case of abdominal laparoscopy, a valve on the proximal portion of the port. Typically, a small incision is made in the skin at a desired location in the patient. The trocar assembly, with the trocar extending out of the port, is then forced through the incision, thereby widening the incision and permitting the port to extend through the incision, past any facie, and into the body (cavity). The trocar is then withdrawn, leaving the port in place. In certain circumstances, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include 5 mm, 10 mm, and 12 mm, which are sized to permit variously sized laparoscopic instruments to be introduced therethrough including, e.g., graspers, dissectors, staplers, scissors, suction/irrigators, clamps, forceps, biopsy forceps, etc. While 5 mm trocar ports are relatively small, in some circumstances where internal working space is limited (e.g., children), it is difficult to place multiple 5 mm ports in the limited area. In addition, 5 mm trocar ports tend to limit movement of instruments inside the abdominal cavity to a great extent.

Further, while laparoscopic surgery has reduced the trauma associated with various surgical procedures and has concomitantly reduced recovery time from these surgeries, there always remains a desire in the art to further reduce the trauma to the patient.

One area of trauma associated with laparoscopic surgery identified by the inventor hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen and inserting the optical device, two incisions for trocar ports for inserting graspers therethrough, and a fourth port for passing a stapler therethrough. Those skilled in the art and those who have undergone surgical procedures that even the 5 mm trocar ports leave holes which must be stitched and which result in scars. Scar tissue may affect the internal portion of the fascia as well as the cosmetic appearance of the skin, which may be detrimental for the patient or even a surgeon if that area of the skin is subject to a later incision or medical procedure.

A second area of trauma associated with laparoscopic surgery relates to trauma resulting from the manipulation (e.g., angling) of the trocar ports required in order to conduct the surgery due to inexact placement. Angling of the port can cause tearing at the incision periphery. Such tearing can lead to extensive scar tissue and in general an extension of the incision area.

A further problem with surgical instruments including a needle tip is inadvertent needle penetration in tissue and resulting scarring or even more serious complications during the surgery if other tissue is nicked or penetrated unintentionally. Therefore a need exists for a surgical instrument or device with an end-effector which controls the needle tip as well.

There continues to be a need in the art for lower cost laparoscopic tools and surgical assemblies which have improved applications, reduce trauma to the patient, reduce complications to the patient, do not lead to extension of the incision area, do not lead to increased scar tissue generation, are easy to make and use, and improve safety while reducing costs to health care providers and patients and reducing the surgical time for a procedure which in turn may reduce costs and complications. The inventive device includes a self-inserting needle assembly which closes over a working tool or end effector, such as a grasping assembling, and thus there is no need for a trocar or other incision point thereby reducing time during the surgical procedure and scarring to the patient at the point of incision.

While conventional needle assemblies including a grasping assembly are known, the conventional art has the grasping assembly actuated by a plunging force out of the needle assembly and retracting back into the needle assembly which may cause tearing of the tissue as the grasping assembly may rotate freely once actuated and out of the needle assembly. Further, when the working tool, of instance a grasping assembly, is fully retracted in the conventional devices, the needle tip may inadvertently penetrated tissue or organs unintentionally. Thus there exists a need for a grasping assembly which is not freely rotational while in use and grasping tissue or other materials. These and other needs are met by the inventive device and method.

Other advantages of the present invention will become apparent from the following description and appended claims.

BRIEF DESCRIPTION OF THE DRAWINGS

FIG. 1 is one embodiment of an unactuated device of the present invention with the graspers in an open position.

FIG. 2 is a top plan view of an embodiment of an unactuated device of the present invention with the graspers in an open position.

FIG. 3 is an embodiment of the grasping assembly of the present invention with the graspers in an open position.

DETAILED DESCRIPTION OF THE PREFERRED EMBODIMENTS

Figure 4:
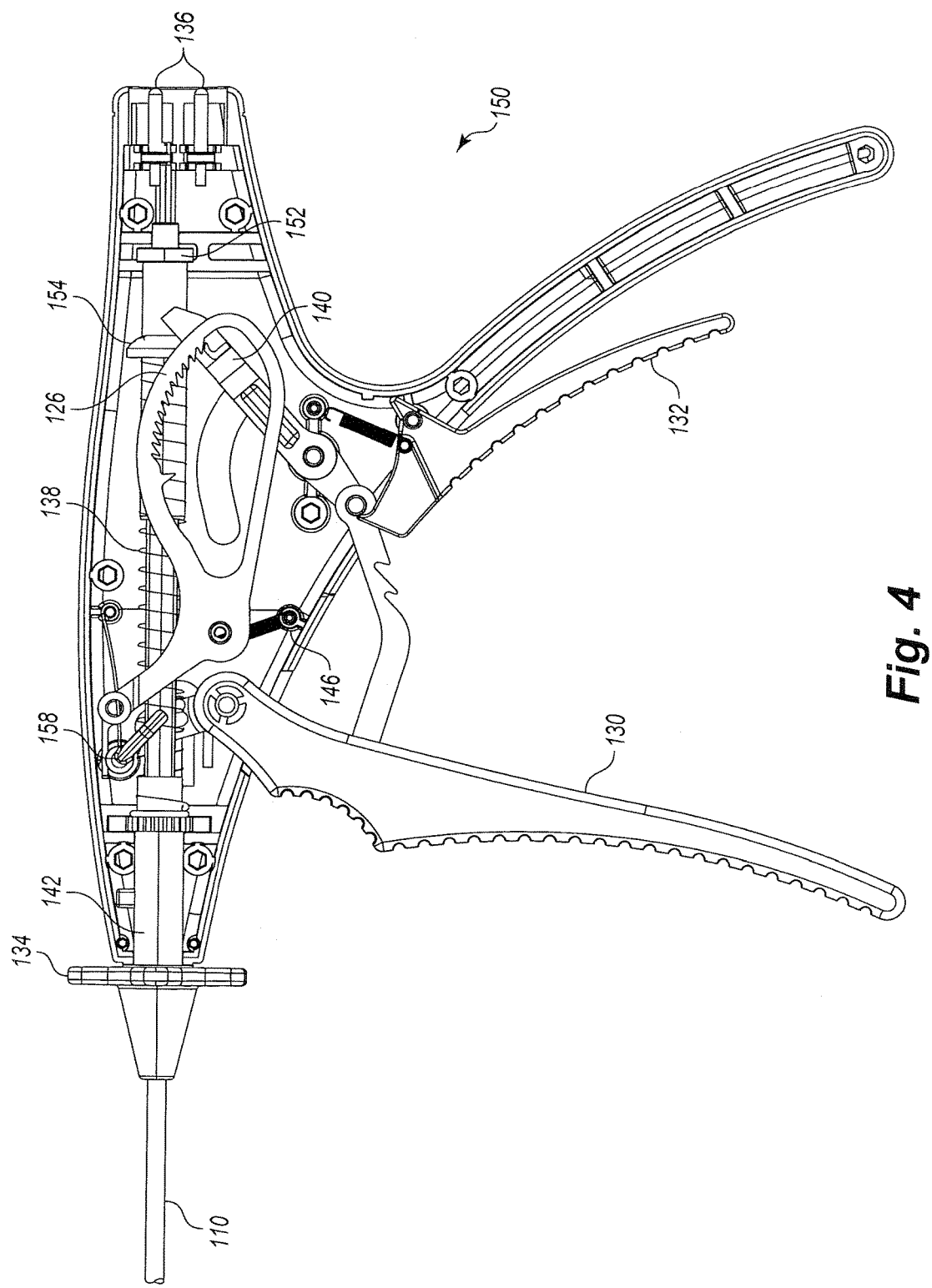
FIG. 4 is an embodiment of the handle assembly of the present invention and a proximal portion of the needle assembly of the present invention.

Reference will now be made to the drawings wherein like reference numerals identify similar structural features or aspects of the subject invention. For purposes of explanation and illustration, and not limitation, exemplary embodiments of a minimally invasive surgical assembly in accordance with the invention, or aspects thereof, are shown in FIGS. 1-7. The surgical assembly of the invention is a low cost, easy to manufacture, medical device which can be used, for example, during minimally invasive surgical procedures to reduce trauma to a patient.

Examples of minimally invasive surgical assemblies and related equipment are described in U.S. Pat. No. 7,766,937 to Ravikumar, U.S. Pat. No. 8,230,863 to Ravikumar et al., U.S. Pat. No. 8,313,507 to Ravikumar, U.S. Pat. No. 8,133,255 to Ravikumar et al., U.S. patent application Ser. No. 11/685,522 to Ravikumar et al (published as U.S. Patent Pub. No. 2007/0250112), U.S. patent application Ser. No. 12/503,035 to Ravikumar (published as U.S. Patent Pub. No. 2010/0016884), U.S. patent application Ser. No. 12/689,352 to Ravikumar et al (published as U.S. Patent Pub. No. 2010/0292724), U.S. patent application Ser. No. 11/610,746 to Ravikumar et al (published as U.S. Patent Pub. No. 2007/0282170), and U.S. patent application Ser. No. 12/689,352 to Ravikumar et al (published as U.S. Patent Pub. No. 2010/0292724), all of which patents, applications, and publications are incorporated by reference herein in their entireties.

The present invention includes a surgical device 100 which includes an elongated needle assembly 110 and a handle assembly 150. The surgical device is shipped to the user (e.g., surgeon) connected and sterilized ready for use during a surgery. The surgical device has the advantage of being self-inserting so that it forms an incision into the fascia of the patient thereby reducing trauma to the patient and eliminates the need for a larger incision point. The incision point may be 5 mm or less depending on the diameter of the distal tip portion 115 of the elongated needle assembly 110 when the elongated needle assembly 110 is actuated and the distal tip portion 115 forced over the working tool assembly, in one embodiment of the present invention as shown in FIG. 1 the working tool assembly is a grasping assembly 120, thereby closing the upper grasper 122 and lower grasper 124.

Referring now to FIGS. 1-3, surgical device 100 is shown including an exploded view of the grasping assembly 120. Surgical device 100 includes an interior lumen longitudinally therethrough. Elongated needle assembly 110 further includes a sharpened distal tip portion 115. In one embodiment of the present invention plastic overwrap 128 is disposed around the proximal end of the needle body of the elongated needle assembly 110 to provide an attachment and rotating point within handle assembly 150 as described below.

Referring now to FIG. 3, grasping assembly 120 is operatively associated with the interior lumen of needle body of the elongated needle assembly 110. Grasping assembly 120 consists of a shaft having an outer surface profile corresponding to an interior surface of the interior lumen of the needle body of the elongated needle assembly 110, and a pair of arms or graspers consisting of an upper grasper 122 and lower grasper 124. The upper and lowers graspers 122, 124 are biased radially outward from the longitudinal axis of the shaft of the needle body of the elongated needle assembly 110.

When assembled within the needle body of the elongated needle assembly 110, lower grasper 124 is maintained in a fixed axial alignment with sharpened distal portion 115 of the needle body of the elongated needle assembly 110 such that upper and lower graspers 122, 124 act as an obturator relative to sharpened distal tip portion 115 of elongated needle assembly 110 to guard the sharpened distal tip portion 115 from causing accidental needle tip trauma to the patient. The fixed axial alignment is maintained by the interaction of a sliding interference between an inner fixed shape, such as an inner rectangular shape, of the overwrap 128 corresponding with an outer fixed shape, such as an outer rectangular shape, of grasping assembly overwrap and similar shape, such as a rectangular shape, of a guide box 142 within the handle assembly 150, as seen in FIGS. 4 and 5.

Figure 5:
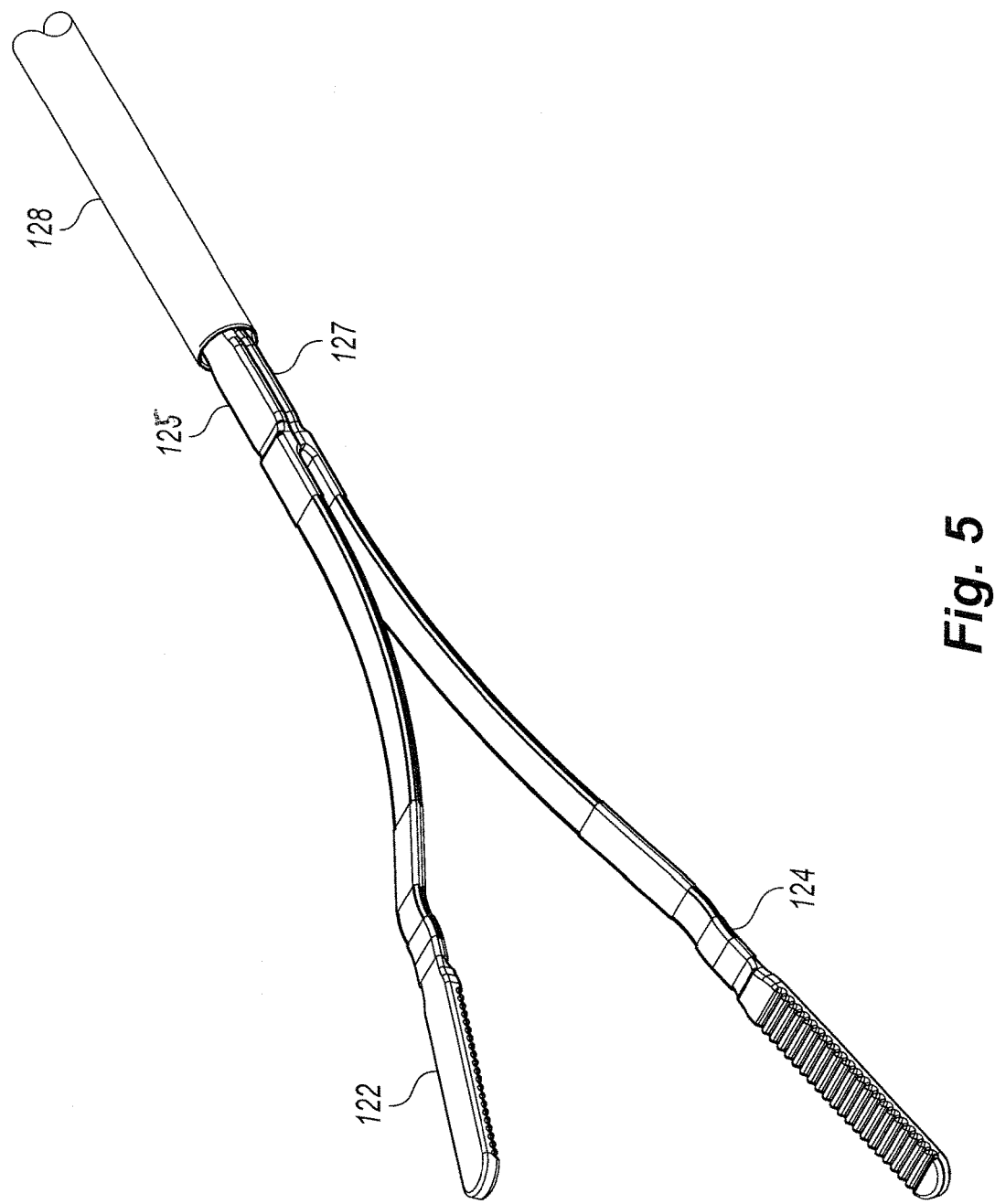
FIG. 5 is an embodiment of a conductive grasping assembly of the present invention with the graspers in an open position.
Figure 6:
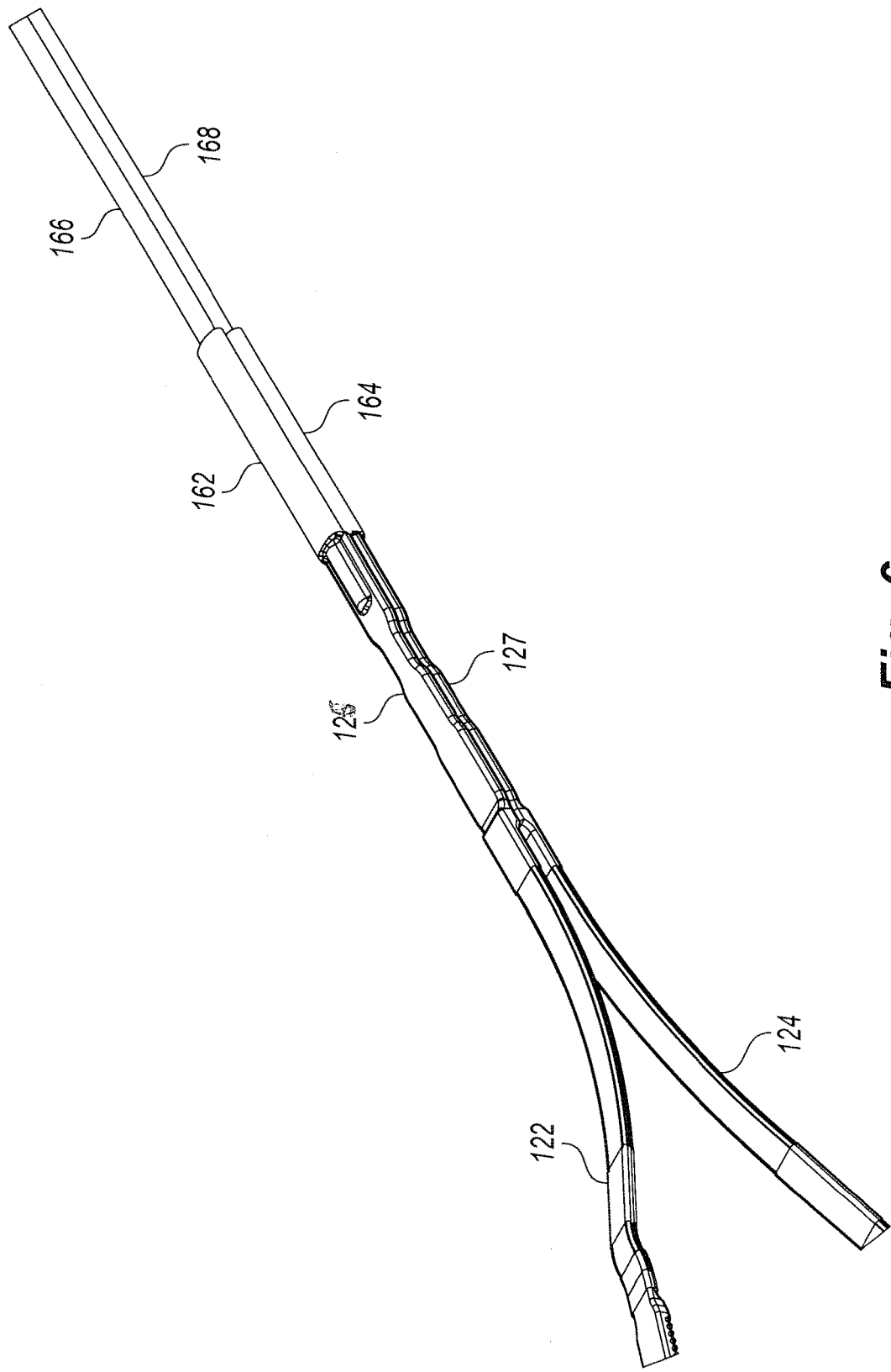
FIG. 6 is another embodiment of a conductive grasping assembly of the present invention with the graspers in an open position.

Referring now to FIG. 4, handle assembly 150 is shown operatively attached to the proximal end portion of the elongated needle assembly 110 (and the shaft within such elongated needle assembly 110) so that the entire elongated needle assembly 110 can be rotated independent of the handle assembly 150. Rotation knob 134 is provided to aide in rotation of the elongated needle assembly 110 and grasping assembly 120. Rotation notch 132 allows rotation of the grasping assembly 120 while simultaneously preventing extension or retraction of grasping assembly 120. In use, the rotation knob 134 may rotate up to 358° so that it does not continuously rotate with such rotation limited so as to prevent the wiring within the bipolar needle assembly 110 from being intertwined and caught. As a safety advantage the rotation knob 134 includes an audible clicking sound so that the user (e.g., surgeon) is aware that the elongated needle assembly 110 is being rotated.

Needle advancement notch 154 is provided on contact with elongated needle assembly 110 to allow both rotation and extension and retraction of elongated needle assembly 110 through the combination of lock knob 158, spring 138 and plunger 140. In operation, the lock knob 158 is moved into the unlocked position and actuator handle 130 is moved in the backward or compressed direction, plunger 140 interacts with needle advancement notch 154 to compress spring 138 thereby extending elongated needle assembly 110 in the forward direction to move towards upper and lower graspers 122, 124 which causes the graspers to close. Spring 138 biases elongated needle assembly 110 towards the reacted position, wherein upper and lower graspers 122, 124 close, helping to prevent accidental needle tip trauma during operation of the surgical device 100.

When actuator handle 130 is moved in the backward or compressed direction to a fully compressed position, needle tip or sharpened distal tip portion 115 is allowed to be exposed for insertion into a patient, and a flag is visible outside of the handle assembly 150 to visually warn the user (e.g., surgeon) that sharpened distal tip portion 115 is exposed. Further, when actuator handle 130 is moved in the backward or compressed direction, tab 146 is moved in the forward direction and prevents rotation of rotation knob 134, elongated needle assembly 110, and grasping assembly 120. By preventing rotation, the torque applied by a user to actuator handle 130 is able to be transferred to upper and lower graspers 122, 124 when in a closed position.

In one embodiment of the present invention, ratchet 126 can be selectively enabled by selector switch. When enabled, ratchet 126 allows a user to move actuator handle 130 to a desired position where the position is held until ratchet 126 is disengaged. Alternatively, when selector switch is not engaged, actuator handle 130 is freely movable throughout the range of motion desired by a user.

In one embodiment of the present invention, shipping handle 132 is provided to store surgical device 100 before use in a desired storage position. Further, shipping handle 132 can be used to extend and hold needle tip, sharpened distal tip portion 115, past upper and lower graspers 122, 124 to provider eased of insertion of surgical device 100 into a patient.

Referring now to FIG. 5, grasping assembly 120 is shown. In an exemplary embodiment, upper and lower graspers 122, 124 are initially formed separate from rods 125, 127 and attached by means, such as epoxy resin or other suitable attachment means. In another embodiment, upper and lower graspers 122, 124 are formed as a pair of electrically isolated conductors. For example, in FIG. 6, rod 125 connects upper grasper 122 to conductor 166. Further, rod 127 connects lower grasper 124 to conductor 168. In such an embodiment the plastic overwrap may be separate for each grasper as shown in overwraps 162, 164. Thus grasping assembly 120 is bipolar in that it is electrically conductive to provide cauterization by the use of upper and lower graspers 122, 124. In an alternate embodiment, other end-effectors or working tools may be used instead of graspers, such as a blunt tip may be used in place of upper and lower graspers 122, 124 to provide a single electrical conductor to a treatment site.

In another exemplary embodiment, grasping assembly 120 can be formed from a unitary rod and upper and lower graspers 122, 124 are etched from the unitary rod wherein the pair of upper and lower graspers 122, 124 and the shaft are formed from a unitary shaft stock.

As can be appreciated, depending on the cutout, any desirable shape of upper and lower graspers 122, 124 can be formed to be used, including for example, a surgical grasper, a lung clamp, and a retractor. Further if the working tool assembly is a grasping assembly 120, the grasping assembly may be in the shape of alligator jaws, babcock jaws, clutch jaws, bowel style jaws and other known variants.

If the elongated needle assembly 110 is bipolar it is energized for surgery. A typical electrosurgical treatment instrument is capable of treating tissue with the use of heat produced by electrical energy while cutting, shearing, grasping, or contacting the tissue. Such instruments are used to carry out treatments, such as incision, coagulation, and the like. During such a procedure instrument or device would be equipped with an active electrode and an inactive, so-called neutral electrode. If monopolar then during the whole duration of the surgery, the neutral electrode is electrically connected to a large area of the skin of the patient, for example, to the thigh or the upper arm.

The surgical instrument interface may further comprise an electrical connector for connecting the conductor to an external electrosurgical generator. Electrical energy may be supplied to the surgical instrument by a conventional electrosurgical which the user (e.g., surgeon) may activate via a foot switch electrically connected to the electrosurgical generator, causing the generator to supply electrical energy through a power cord and the connector to the instrument. Typically a high frequency AC or RF current may be employed, with the voltage being dependent on the type and degree of treatment desired. Voltages may range up to at least 12,000V in some cases, with about 3000V being a typical value, e.g., for coagulation.

Figure 7:
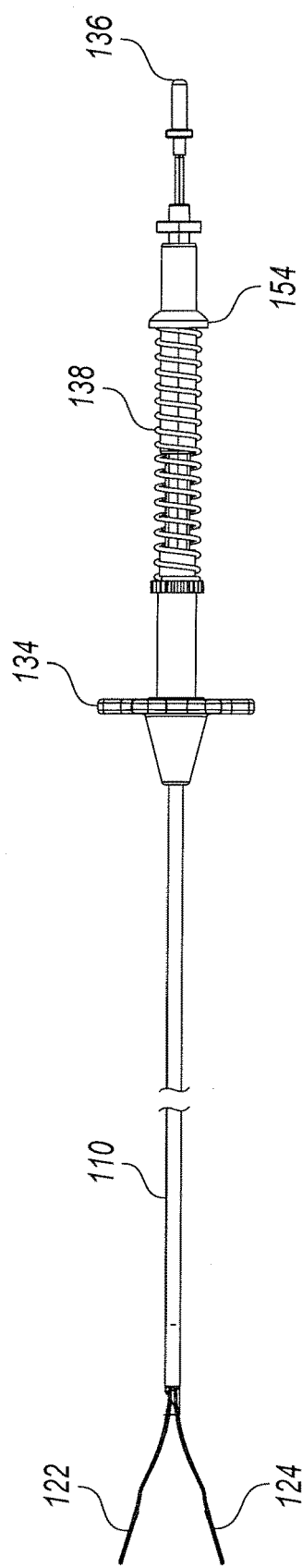
FIG. 7 is an embodiment of the present invention.

As shown in FIGS. 4 and 7, the inventive device includes a contact post 136, or a multiple of contact posts 136, connected to an electrical source as described above.

The inventive device has the advantage of being a needle-scopic instrument with a small diameter (approx. 3 mm or less, preferably 2.3 mm or less) that is mainly comprised of a needle and a rod with jaw end-effectors. The needle has percutaneous ability to enter the body cavity and thus does not require entry through a trocar, thus reducing the trauma to the patient with smaller incision point and possibly less incisions in aggregate during the surgery.

The access insertion needle allows for time-saving entry into a patient's body, for example into the abdominal cavity, and also eliminates single incision closure at the end of each procedure. The inventive device's ultra slim design and incisionless entry capabilities can help reduce patient scarring.

Notably the inventive device has end effectors that are spring-biased and are closed by actuation of the outer needle. Thus there are additional safety features for the inventive device such as closure of the needle over the end-effectors, for instance open jaws, which add force to closing the open jaws and thus securing the tissue more forcibly. Further, as the jaws are closed there is less occurrence of accidental needle trauma to the patient.

A further advantage of the present invention is that the needle tip, such as the sharpened distal tip portion 115, is always in rotational alignment with the working tool or end effectors, such as the grasping assembly 120. Thus the surgeon is assured of the rotational alignment of the end effectors when moving the handle assembly 150 and the entire surgical device 100.

In addition, the stainless steel instrumentation tip and stabilizing pivot disk of the inventive device provide maximum strength to secure, retract and manipulate human tissue and organs. Depending on the chosen end-effector to the needle assembly the inventive device may be used for percutaneous access in a wide variety of laparoscopic procedures. In another embodiment of the present invention the sharpened distal tip portion 115 could be blunt, beveled shaped or other shapes.

A further safety feature of the present invention includes the ratchet 126 having audible and tactile clicks during actuation. The ratchet 126 may have a minimum of for instance a range of about three (3) to about ten (10) lock positions throughout the full graspers 122, 124 closure stroke. The final ratchet 126 position may correspond with the fully closed grasping assembly 120 overlaid with the sharpened distal tip portion 115. In one embodiment of the present invention, a ratchet switch will allow the ratchet 126 to be turned on and off to disengaged the ratchet 126 and allow free opening of the grasping assembly 120, or any other assembly with other end effectors, upon manual release of the actuator handle 130 by the user. The ratchet switch may reside on both sides of the handle assembly 150 and thus may be actuated with the thumb of the user. In one embodiment of the present invention the up switch position of the ratchet switch corresponds with the ratchet mode while the down position corresponds to the free mode. A ratchet spring will drive the ratchet switch to either its final ratchet position or free position so as to prevent the ratchet switch from residing in an intermediate position. Such ratchet switch actuation may have an audible and tactile click as a further safety feature for the user. In one embodiment of the present invention a temporary ratchet release trigger may reside forward of the actuator handle 130 and may be actuated by the index finger of the user. Such a temporary release trigger will allow the ratchet 126 to be released when the release trigger is squeezed during the time in use when the device is in the ratchet 126 mode. Such an embodiment may have a spring return and will reengage the ratchet 126 when the temporary release trigger is released.

Further advantages include retention of abdominal pressure during an abdominal surgery. Also the inventive device when in use during a surgery may be self-sealing without compromising insufflation pressure. Finally, there is, for the surgeon when in use, a previously unknown entry-depth control through retention and pivot disc of the inventive device.

The following benefits, structure, and advantages are also contemplated by the present invention: reduced surgical time resulting in reduced trauma to the patient and possibly less scarring, easier handling of the device by the user via the locked rotational hub and multiple types of end-effectors, and other benefits.

The methods and systems of the present invention, as described above and shown in the drawings, provide for minimally invasive surgical assemblies with superior properties including ease of assembly, use and operation. While the apparatus and methods of the subject invention have been shown and described with reference to preferred embodiments, those skilled in the art will readily appreciate that changes and/or modifications may be made thereto without departing from the spirit and scope of the subject invention.

LISTING OF NUMERALS

- 100 surgical device
- 110 elongated needle assembly
- 115 sharpened distal tip portion
- 120 grasping assembly
- 122 upper grasper
- 124 lower grasper
- 125 rod
- 126 ratchet
- 127 rod
- 128 overwrap
- 130 actuator handle
- 132 shipping handle
- 134 rotation knob
- 136 contact post
- 138 spring
- 140 plunger
- 142 guide box
- 146 tab
- 150 handle assembly
- 152 rotation notch
- 154 needle advancement notch
- 158 lock knob
- 162 overwrap
- 164 overwrap
- 166 conductor
- 168 conductor

What is claimed is:

1. A surgical device, comprising:
    a) an elongated needle body defining an interior lumen extending longitudinally therethrough, the elongated needle body having a sharpened distal tip portion;
    b) an assembly operatively associated with the interior lumen of the elongated needle body, the assembly having:
        i) a shaft having an outer surface profile corresponding to an inner surface of the interior lumen of the elongated needle body; and
        ii) a pair of arms extending distally from the shaft, each of the pair of arms comprising a rod and a grasper, wherein the graspers are biased radially outward from the longitudinal axis of the shaft, and one arm of the pair of arms is in a fixed axial alignment with the sharpened distal tip portion of the elongated needle body such that the pair of arms act as an obturator relative to the sharpened distal tip portion of the elongated needle body to guard the elongated needle body from causing accidental needle tip trauma; and
    c) a handle portion operatively attached to a proximal end portions of both the elongated needle body and the shaft such that the elongated needle body and the shaft can be rotated independent of the handle portion, the handle portion further configured and adapted to advance and retract the elongated needle body over the pair of arms and the shaft, the elongated needle body being biased towards a retracted position to further guard the elongated needle body from accidental needle trauma,
    wherein the pair of arms are formed as electrically isolated conductors, and
    wherein the rods are each encircled by a plastic overwrap, the plastic overwrap having a shape corresponding to a respective outer surface of the rods to maintain the fixed axial alignment.

2. The surgical device of claim 1, wherein the handle portion is configured to prevent rotation of the elongated needle body and the assembly when the pair of arms are positioned toward a closed position by the extension of the elongated needle body.

3. The surgical device of claim 1, wherein the handle portion further comprises a selectively enabled ratchet mechanism.

4. The surgical device of claim 1, wherein the handle portion further comprises a needle armed indication.

5. The surgical device of claim 1, further comprising a rotation hub connected with the elongated needle body and the handle portion configured to have rotational alignment when in a locked position.

6. The surgical device of claim 1, further comprising a safety mechanism establishing a working range for said elongated needle body relative to a grasping assembly formed by the pair of arms,
    wherein said working range, said pair of arms may extend past the sharpened distal tip portion of said elongated needle body, and said safety mechanism includes a stop which prevents said sharpened distal tip portion from extending past said pair of arms.

7. The surgical device of claim 1, wherein the pair of arms are configured as a surgical grasper.

8. The surgical device of claim 1, wherein the pair of arms are configured as a lung clamp.

9. The surgical device of claim 1, wherein the pair of arms are configured as a retractor.

10. The surgical device of claim 1, further comprising a rotation knob to aid in rotation of the elongated needle body, wherein the rotation knob is configured to rotate up to 358° and not rotate continuously beyond.

11. A surgical method comprising:
  a) obtaining a surgical device having (i) an elongated needle body defining an interior lumen extending longitudinally therethrough, the elongated needle body having a sharpened distal tip portion; (ii) an assembly operatively associated with the interior lumen of the elongated needle body, the assembly having a shaft having an outer surface profile corresponding to an inner surface of the interior lumen of the elongated needle body; and a pair of arms extending distally from the shaft, each of the pair of arms comprising a rod and a grasper, wherein the graspers are biased radially outward from the longitudinal axis of the shaft, and one arm of the pair of arms is in a fixed axial alignment with the sharpened distal tip portion of the elongated needle body such that the pair of arms act as an obturator relative to the sharpened distal tip portion of the elongated needle body to guard the elongated needle body from causing accidental needle tip trauma; and (iii) a handle portion operatively attached to proximal end portions of both the elongated needle body and the shaft such that the elongated needle body and shaft can be rotated independent of the handle portion, the handle portion further configured and adapted to advance and retract the elongated needle body over the pair of arms and the shaft, the elongated needle body being biased towards a retracted position to further guard the elongated needle body from accidental needle trauma, wherein each arm of the pair of arms is mounted to the distal portion of the shaft, and wherein the pair of arms are formed as electrically isolated conductors, the rods are each encircled by a plastic overwrap, the plastic overwrap having a shape corresponding to a respective outer surface of the rods to maintain the fixed axial alignment;
  b) with the pair of arms in a closed position, using the sharpened distal tip portion for insertion of the surgical device into a cavity of a patient;
  c) moving an actuator handle backward relative to the elongated needle body to cause the sharpened distal tip portion to retract allowing the pair of arms to open relative to each other;
  d) moving the pair of arms over an object in the cavity; and
  e) moving the sharpened distal tip portion of the elongated needle body forward relative to the pair of arms to cause the pair of arms to close over said object.

12. The method according to claim 11, further comprising: pushing or pulling the object by moving the actuator handle.

13. The method according to claim 11, further comprising: releasing the object by moving the sharpened distal tip portion of the elongated needle body backward relative to the surgical device to permit the pair of arms to automatically open relative to each other.

14. The method according to claim 11, further comprising: withdrawing the surgical device from the cavity.

15. The method according to claim 11, further comprising: supplying electrical energy to the surgical device while the pair of arms are closed over the object.

* * * * *